US012115078B2

(12) United States Patent
Dimitroulis et al.

(10) Patent No.: US 12,115,078 B2
(45) Date of Patent: Oct. 15, 2024

(54) REPLACEABLE FOSSA COMPONENT FOR A TEMPOROMANDIBULAR JOINT REPLACEMENT SYSTEM

(71) Applicant: MAXONIQ Pty Ltd, Carlton (AU)

(72) Inventors: George Dimitroulis, Carlton (AU); Chris McCrowe, Carlton (AU)

(73) Assignee: MAXONIQ Pty Ltd, Carlton (AU)

( * ) Notice: Subject to any disclaimer, the term of this patent is extended or adjusted under 35 U.S.C. 154(b) by 119 days.

(21) Appl. No.: 17/356,478

(22) Filed: Jun. 23, 2021

(65) Prior Publication Data

US 2022/0409377 A1 Dec. 29, 2022

(51) Int. Cl.
*A61F 2/30* (2006.01)

(52) U.S. Cl.
CPC .. *A61F 2/3099* (2013.01); *A61F 2002/30159* (2013.01); *A61F 2002/30991* (2013.01); *A61F 2310/00023* (2013.01)

(58) Field of Classification Search
CPC .......... A61F 2/3099; A61F 2002/30991; A61F 2002/30993; A61F 2002/30387; A61F 2310/30433; A61F 2002/30383–30401
See application file for complete search history.

(56) References Cited

U.S. PATENT DOCUMENTS

| 5,405,393 | A | * | 4/1995 | Falkenstrom | A61F 2/3099 623/17.17 |
| 5,549,680 | A | * | 8/1996 | Gordon | A61F 2/3099 623/17.17 |
| 6,132,466 | A | * | 10/2000 | Hoffman | A61F 2/3099 623/17.17 |
| 2011/0184527 | A1 | * | 7/2011 | Vanasse | A61F 2/42 623/21.15 |
| 2016/0081806 | A1 | * | 3/2016 | Dubois | A61F 2/4603 623/17.17 |

* cited by examiner

*Primary Examiner* — Javier G Blanco
(74) *Attorney, Agent, or Firm* — Davison IP; Scott H. Davison

(57) ABSTRACT

A temporomandibular joint replacement system includes a condylar component secured with a mandibular bone and a fossa component with a fossa backing secured with a zygomatic bone and slidably attached with a removable fossa lining, the fossa lining having an open-ended concave fossa dome with a post-center peak to allow for mediolateral and anterior translation with a rounded, oblong condylar head of the condylar component. The slidable attachment mechanism of the fossa backing and fossa lining is laterally-oriented to allow for post-implantation removal and replacement without disturbing any bone or bone-interfacing components. The bone-interfacing surfaces are anatomically-contoured to their respective bone surfaces and formed with materials and textures which promote osseointegration with the joint replacement.

6 Claims, 16 Drawing Sheets

REPLACEABLE FOSSA COMPONENT FOR A TEMPOROMANDIBULAR JOINT REPLACEMENT SYSTEM

BACKGROUND

Field of the Invention

The embodiments described herein are related to temporomandibular joint replacements, and more particularly to a temporomandibular joint prosthesis with a two-part fossa component which can be removed and replaced after implantation.

Related Art

The temporomandibular joint (TMJ) is a joint connecting the temporal bone of the skull to the mandibular bone of the jaw. The joint is complex, allowing for both anterior and posterior movement as well as mediolateral movement. This movement is generally accomplished by the interaction between a condylar head of the mandibular bone and a glenoid fossa of the temporal bone.

For a variety of reasons, the TMJ often wears down or fails—due to aging, accidents, disease or other physiological issues. In severe cases, it becomes necessary to replace the TMJ with a prosthesis which attempts to mimic the functionality and movement of the joint. This is exceedingly difficult due not only to the complexity of the joint itself, but to the desired movement in the mediolateral and anterior directions, along with the need for the joint to work with its corresponding joint on the opposite side of the jaw.

As a result of this complexity, TMJ replacements are often minimally effective at replacing and mimicking the TMJ. The replacement components which make up the condylar head and glenoid fossa often wear down, degrade or fail over time, requiring replacement of one or more of the prosthetic components. Replacement of a component which has been secured to the remaining bone structure is complex and often not possible. Additionally, the osseointegration of the existing prosthesis with the bone makes removal of failed prosthetic components even more difficult and unlikely.

Recent improvements in additive manufacturing have led to the development of customizable TMJ implants which have significantly improved upon the prior issues with regard to functionality, materials and movement. However, existing implants still struggle to provide sufficient structural support while avoiding complications from failure of the implant to osseointegrate with the bone or allow tissue to reattach with bone structure around the implant. Failure of the interface between the condylar head and articulating surface of the fossa remain inevitable due the type of movement required and the amount of wear and tear experienced by the surfaces over time.

SUMMARY

Embodiments of a temporomandibular joint replacement system described herein include a condylar component secured with a mandibular bone and a fossa component with a fossa backing secured with a zygomatic bone and slidably attached with a removable fossa lining, the fossa lining having an open-ended concave fossa dome with a post-center peak to allow for mediolateral and anterior translation with a rounded, oblong condylar head of the condylar component. The slidable attachment mechanism of the fossa backing and fossa lining is laterally-oriented to allow for post-implantation removal and replacement without disturbing any bone or bone-interfacing components. The bone-interfacing surfaces are anatomically-contoured to their respective bone surfaces and formed with materials and textures which promote osseointegration with the joint replacement.

In one embodiment of the invention, a temporomandibular joint replacement comprises: a condylar component anatomically-contoured for attachment with a mandibular bone and having a condylar head; and a fossa component comprising: a fossa backing anatomically-contoured for attachment with a zygomatic bone; and a fossa lining slidably attached with the fossa backing, the fossa lining including an open-ended concave articulating surface which interfaces with the condylar head.

In another embodiment of the invention, a temporomandibular joint replacement comprises a condylar component anatomically-contoured for attachment with a mandibular bone and having a condylar head, wherein the condylar head has a rounded, oblong shape; and a fossa component anatomically-contoured for attachment with a zygomatic bone and further comprising an open-ended concave articulating surface which interfaces with the condylar head, wherein the articulating surface of the fossa lining curves to a high point posterior of a center of a sagittal plane and apexes at a center of the fossa lining in a coronal plane.

In a further embodiment of the invention, a method of manufacturing a temporomandibular joint replacement comprises the steps of: forming an anatomically-contoured condyle component including a condylar head and a body portion for attachment with a mandibular bone; forming a fossa component including a fossa backing anatomically-contoured for attachment with a zygomatic bone and a fossa lining slidably attached with the fossa backing, the fossa lining including an open-ended concave articulating surface which interfaces with the condylar head.

In a still further embodiment of the invention, a method of replacing a fossa component of a temporomandibular joint replacement comprises the steps of: removing a stabilization screw from a fossa lining and fossa backing of a fossa component; slidably removing the fossa lining from the fossa backing; slidably attaching a replacement fossa lining with the fossa backing; and securing the replacement fossa lining with the fossa backing with the stabilization screw.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Figure 1:
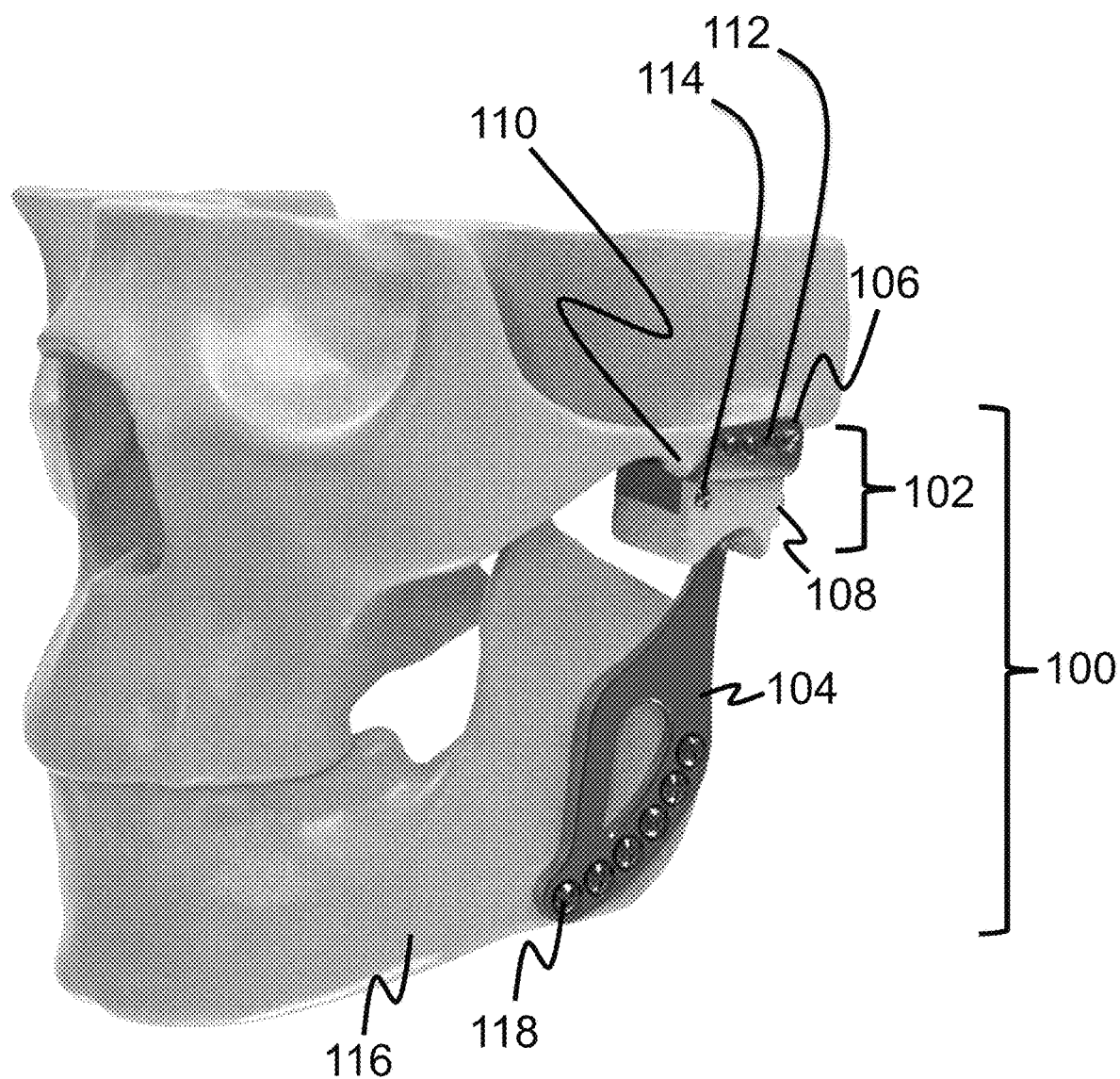
FIG. 1 is a perspective-view illustration of a temporomandibular joint replacement prosthesis attached with a mandibular bone and a zygomatic bone, according to an embodiment of the invention.

Certain embodiments disclosed herein provide for a temporomandibular joint replacement system described herein include a condylar component secured with a mandibular bone and a fossa component with a fossa backing secured with a zygomatic bone and slidably attached with a removable fossa lining, the fossa lining having an open-ended concave fossa dome with a post-center peak to allow for mediolateral and anterior translation with a rounded, oblong condylar head of the condylar component. The slidable attachment mechanism of the fossa backing and fossa lining is laterally-oriented to allow for post-implantation removal and replacement without disturbing any bone or bone-interfacing components. The bone-interfacing surfaces are anatomically-contoured to their respective bone surfaces and formed with materials and textures which promote osseointegration with the joint replacement.

The temporomandibular joint (TMJ) replacement prosthesis replaces the mandibular condyle and augments the glenoid fossa to reconstruct a damaged or diseased TMJ when there is no alternative clinical avenue. The prosthesis is designed to mimic the natural range of motion of the TMJ by providing an articulating surface with a specified curvature that interfaces with an oblong condylar head to provide mediolateral and anterior motion similar to that of the natural joint.

Additionally, the use of fossa component with a sub-assembly of three parts—the fossa backing, fossa lining and stabilization screw—allows for the simple and minimally-invasive replacement of the articulating surface of the fossa if it wears down or does not provide an adequate range of motion over time. The fossa lining can be removed without disturbing the fossa backing or condylar components, thus avoiding disturbing any portions of the prosthesis which are attached with the bone structure. This allows for decreased surgery times and faster recovery by the patient.

This device is intended to be surgically implanted by suitably qualified oral and maxillofacial surgeons and/or plastic surgeons that have completed sufficient bridging training. The device may be used for patients who are typically suffering from intolerable symptoms of pain and/or jaw joint dysfunction who have failed to adequately respond to other treatments. This may include one or more of the following indications: osteoarthritis, other degenerative joint conditions, post-traumatic arthritis, rheumatoid arthritis, psoriatic arthritis, revision surgery, previously failed prosthetic joints, previously failed autogenous grafts, multiple operations on TMJ, developmental abnormalities, ankylosis, condylar hypoplasia, condylar resorption, benign tumors, osteochondroma and chondroma/osteoma.

The TMJ replacement prosthesis may be created using a three-dimensional medical image of a patient's bone structure in order to anatomically contour the implant to the individual patient. The implant may be created electronically via a software program which incorporates a three-dimensional (3D) image of the bone to create a corresponding 3D image of the implant that can then be further customized to create exact measurements of all aspects of the condylar components and fossa components that will fit the patient's anatomy. The implant components may then be additively-manufactured from a biocompatible material as a single piece to maximize the structural stability of the implant.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

I. Temporomandibular Joint Replacement Prosthesis

FIG. 1 is an illustration of one embodiment of a temporomandibular joint (TMJ) replacement prosthesis 100 after implantation. The TMJ replacement 100 primarily comprises a fossa component 102 and a condylar component 104 which are attached to respective portions of the bone structure of a human jaw and provide a replacement condyle and glenoid fossa to mimic the function of the TMJ. In the present embodiment, the fossa component 102 is separated into two components—a fossa backing 106 which is secured to the bone structure, and a fossa lining 108 with a concave articulating surface which interfaces with a condylar head of the condylar component. The fossa lining 108 is slidably attached with the fossa backing 106 to allow for the fossa lining 108 to be quickly and easily removed and replaced after implantation of the TMJ replacement without disturbing any bone or bone-interfacing components. In one embodiment, a stabilization screw 114 may be utilized to secure the fossa backing with the fossa lining during the implantation procedure.

As further illustrated in FIG. 1, the fossa backing 106 is secured with a zygomatic arch of a zygomatic bone 110 via a plurality of bone screws 112. Correspondingly, the condylar component 104 is secured with a ramus of a mandibular bone 116 via a plurality of bone screws 118.

II. Fossa Replacement Component

Figure 2:
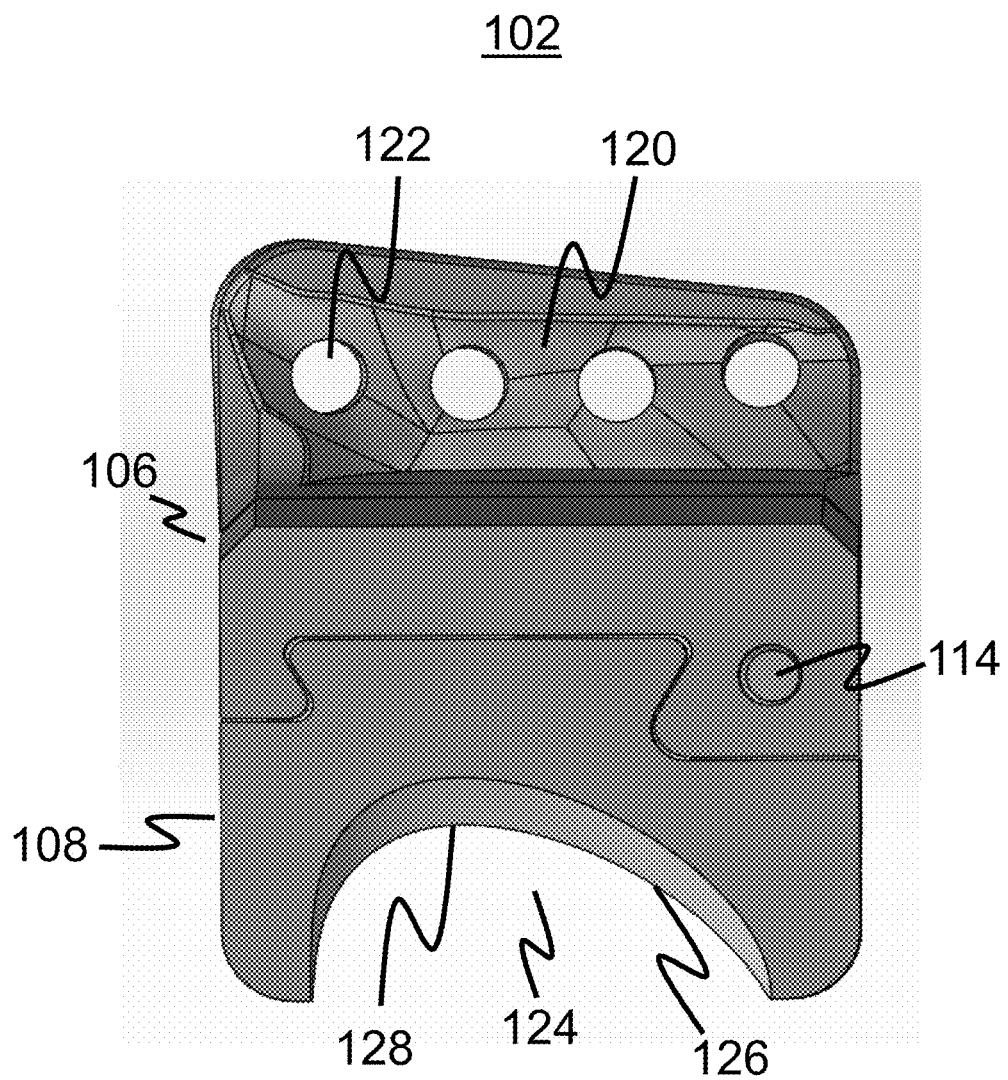
FIG. 2 is a front-view illustration of a fossa component, according to an embodiment of the invention.

FIG. 2 is a detailed front-view illustration of the fossa component including the fossa backing 106 and fossa lining 108 in an attached configuration. The fossa backing 106 includes a flange 120 which protrudes out from the main body and includes a plurality of openings 122 for inserting the bone screws 112 to attach the fossa backing 106 to the zygomatic bone 110. As shown in FIG. 2, the bone-facing surface of the flange 120 may be anatomically-contoured to fit the specific shape of a patient's bone structure to ensure an exact fit between the flange and the bone surface. The stabilization screw 114 is shown in its inserted position to secure the fossa backing 106 with the fossa lining 108.

Also in FIG. 2, the side view shape of the articulating surface 124 of the fossa lining 108 can be shown, which has a distinct articulation point 128 interfacing with a unique, oblong condylar head to provide a similar shape and function as that of a natural TMJ. As shown, an inner surface 126 gradually curves to its highest point 128 posteriorly of a center in the sagittal plane and has its apex at the center of the fossa lining in the coronal plane. This holds the Condylar head in correct occlusion and allows for mediolateral translation and anterior movement.

Figure 3:
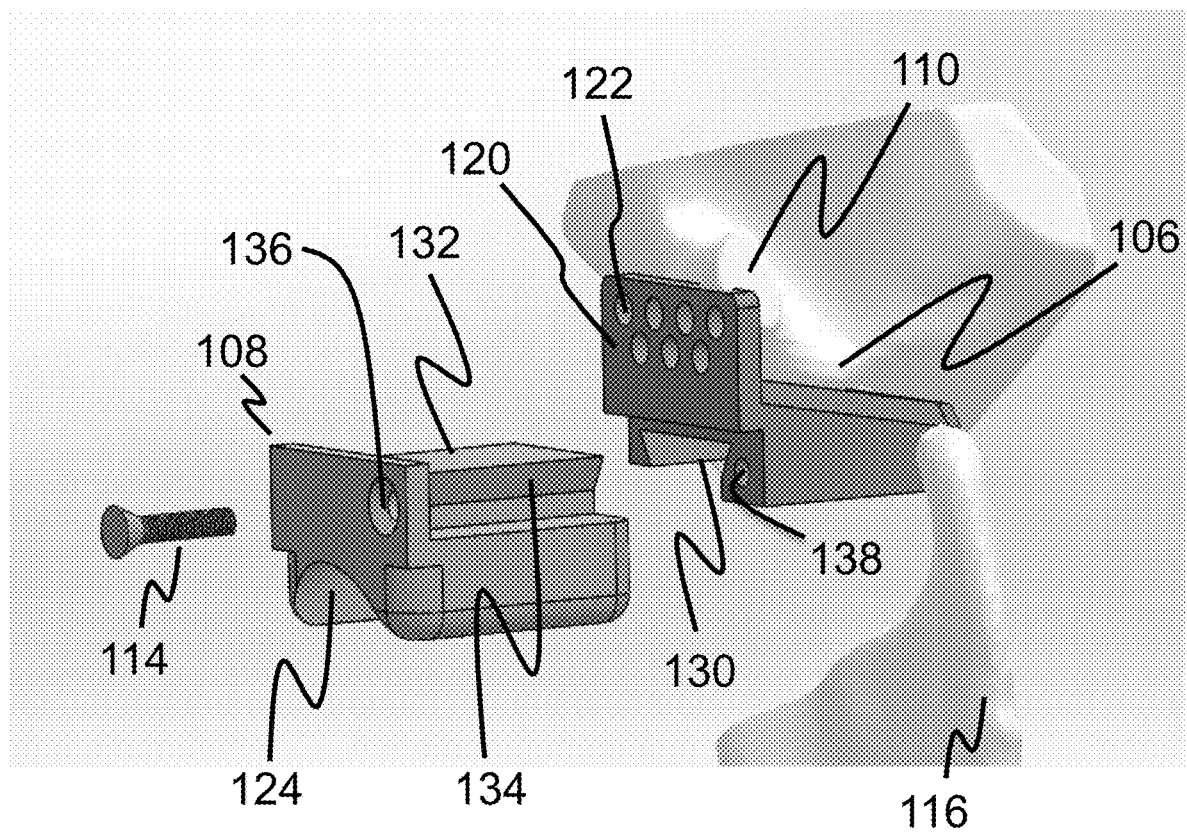
FIG. 3 is an exploded view illustration of the fossa component, according to an embodiment of the invention.

FIG. 3 is an exploded view illustration of the fossa component 102, illustrating the positioning of the fossa backing 106 against the zygomatic bone 110, the fitting of the fossa lining 108 into the fossa backing, and the insertion of the stabilization screw 114 into openings in the fossa backing 106 and fossa lining 108 to secure the component assembly onto the bone. As noted above, the fossa backing 106 includes a plurality of openings 122 in the flange 120 for inserting a plurality of bone screws to attach the fossa backing 106 to the zygomatic arch. The number of openings 122 will vary depending on the particular shape and structure of each individual patient's anatomy but may vary from approximately four to approximately seven. The fossa backing 106 also includes a slot 130 to slidably receive a corresponding tab 132 on the fossa lining, and this sliding mechanism serves as the primary attachment mechanism between the fossa backing 106 and fossa lining 108.

The fossa lining 108 includes a concave, open-face articulating surface 124 on a bottom surface and a tab 132 with a grooved edge 134 which slidably attaches with the slot 130 of the fossa backing 106. Although the interface between the slot 130 and tab 132 substantially secures the fossa components together, a secondary stabilization mechanism may be added to more permanently secure the components, such as the stabilization screw 114. As illustrated in FIG. 3, the stabilization screw 114 may be inserted through a hole 136 in a lateral side of the fossa lining 108 and into a threaded hole 138 in the fossa backing 106 which may extend substantially into the body of the fossa backing 106 to provide maximum stabilization and retention of the fossa lining with the fossa backing.

The lateral movement of the attachment mechanism between the slot 130 and tab 132, as well as the lateral insertion of the stabilization screw 114, will allow for the entire fossa lining 108 to be removed and replaced post-implantation, as will be further described below.

Figure 4:
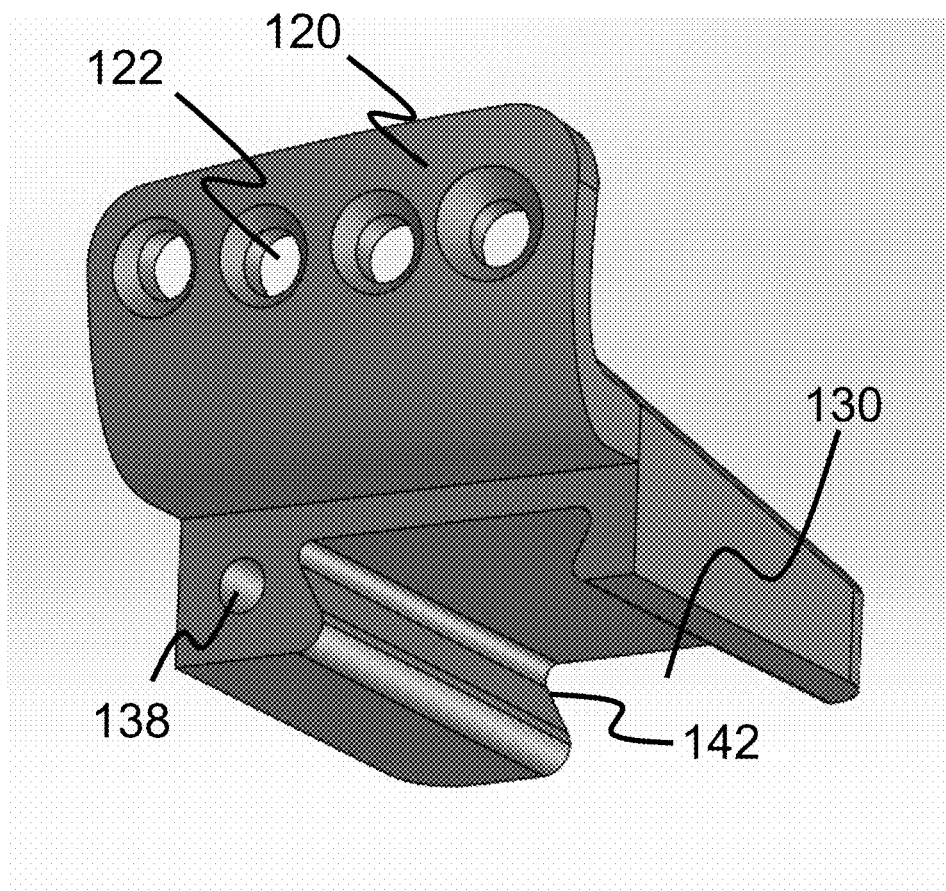
FIG. 4 is a perspective rear-view illustration of a fossa backing, according to one embodiment of the invention.

FIG. 4 is a perspective rear-view illustration of one embodiment of the fossa backing 106 more clearly illustrating the shape of the flange 120 and the slot 130. The slot 130 includes a tapered edge 142 extending inward into the slot 130 which creates a narrower opening designed to retain the corresponding shape of the tab 132 of the fossa lining 108.

Figure 5:
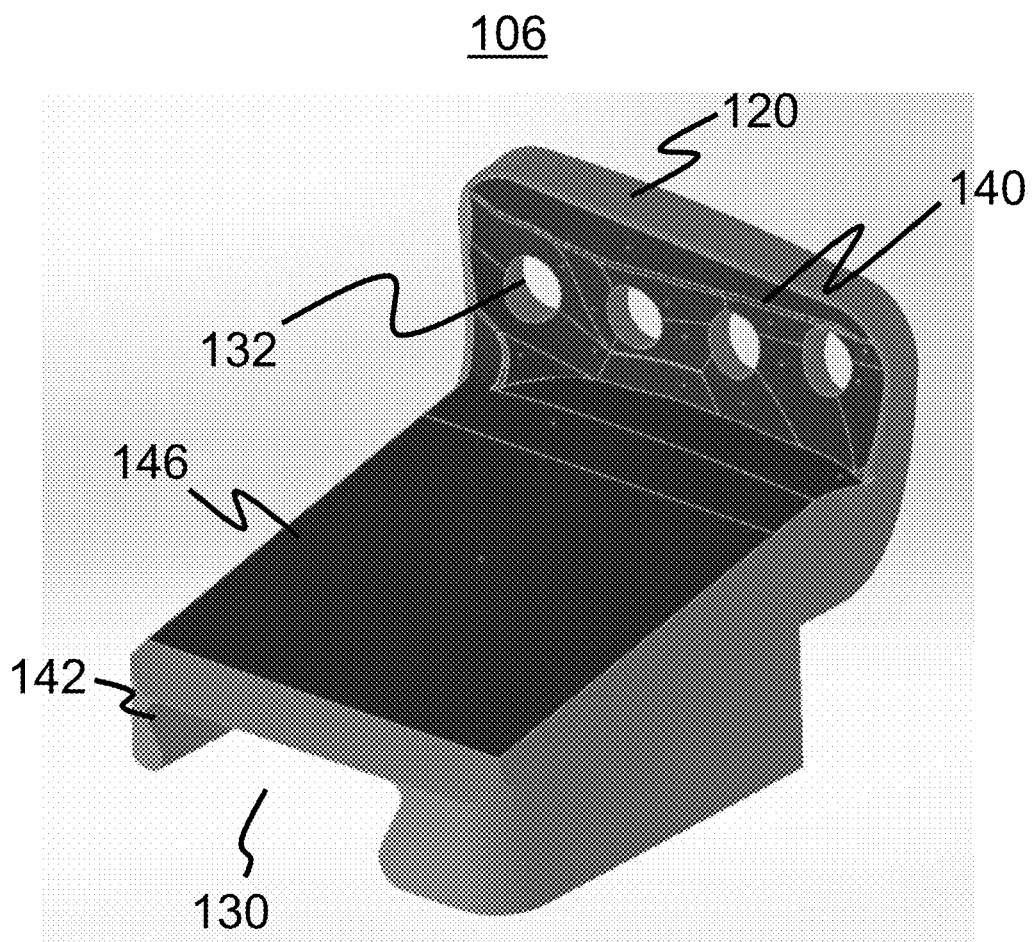
FIG. 5 is a perspective front-view illustration of the fossa backing, according to one embodiment of the invention.

FIG. 5 is a perspective front-view illustration of one embodiment of the fossa backing 106 which more clearly illustrates how an interior, bone-facing surface 140 of the flange 120 is designed to fit a contour of an individual patient's zygomatic arch based off of a CT scan taken of the bone shape. The bone-facing surface 140 and a seat portion 146 of the fossa backing 106 may be manufactured with a roughened surface to encourage osseointegration with the native bone. The tapered edge 142 of the slot 130 is also shown, indicating that the tab 132 of the fossa lining 108 extends the entire length of a lower surface of the fossa backing 106 in order to provide sufficient retention and stability of the fossa component 102.

Figure 6:
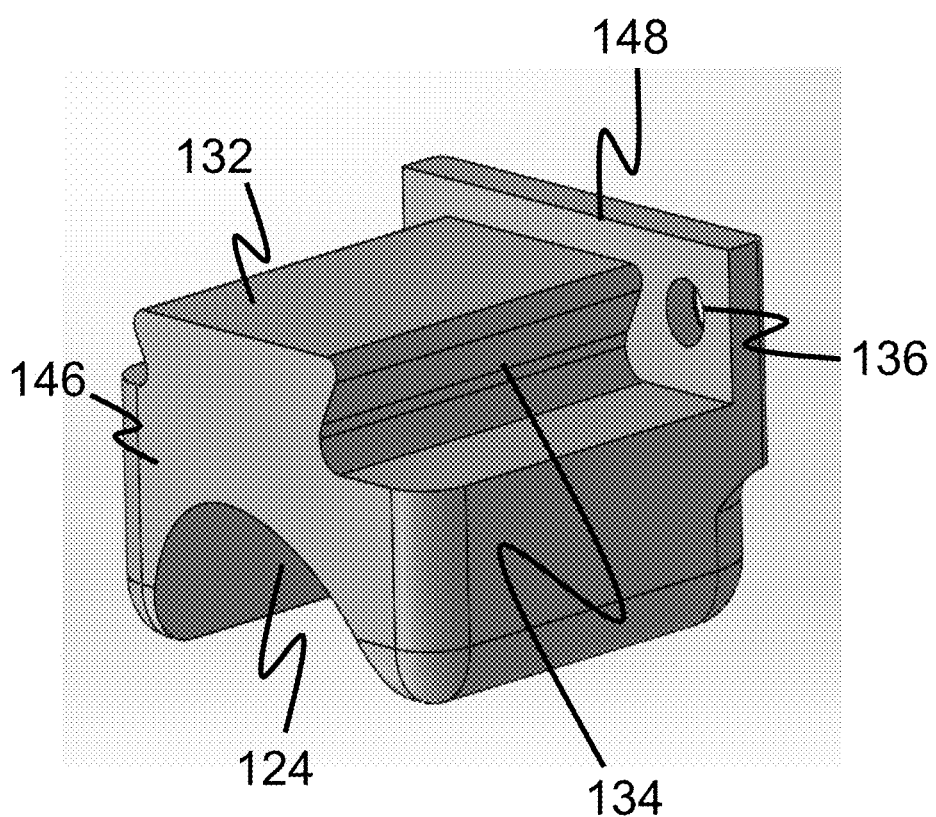
FIG. 6 is a perspective front-view illustration of a fossa lining, according to an embodiment of the invention.

FIG. 6 is a perspective front-view illustration of one embodiment of the fossa lining 108, more clearly illustrating a grooved edge 134 of the tab 132 which is shaped to fit into the tapered edge 142 of the fossa backing 106. The fossa lining is configured to slide laterally into the slot 130 of the fossa backing 106 and lock into place to prevent forward movement, with the stabilization screw 114 retaining the fossa backing 106 and fossa lining 108 laterally in position. The fossa lining also includes a flange portion 148 with the hole 136 for receiving a tapered head of the stabilization screw 114. The inferior surface of the fossa lining 108 includes the concave articulating surface 124 which interfaces with the condylar head of the condylar component 104 and extends the entire length of the inferior surface, from the fossa flange 148 on a back end to a front end 146.

Figure 7:
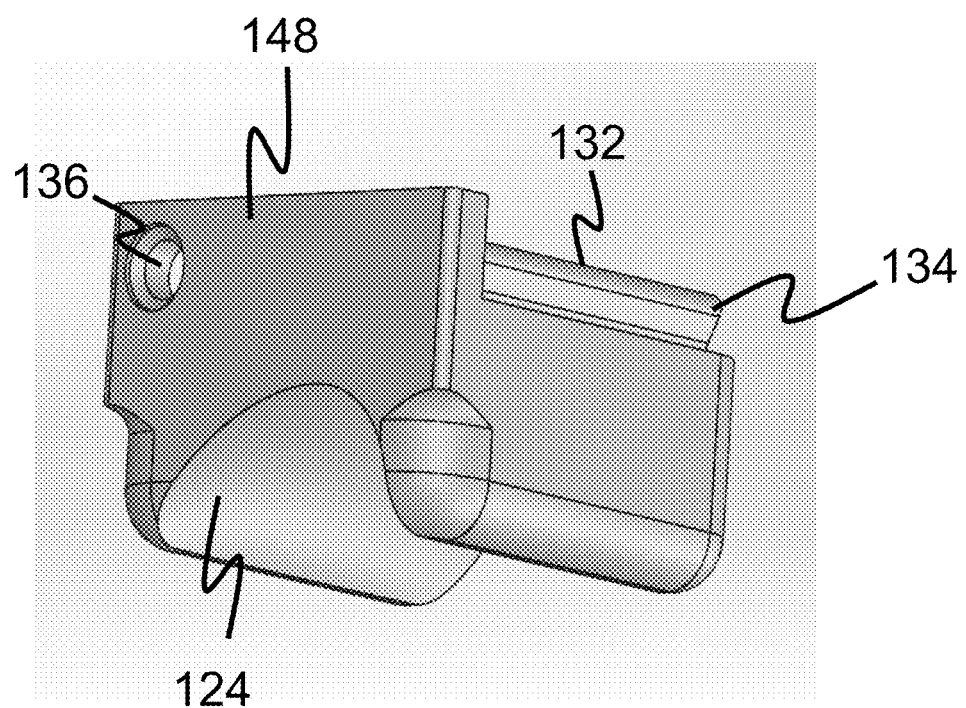
FIG. 7 is a perspective rear-view illustration of the fossa lining, according to an embodiment of the invention.

FIG. 7 is a perspective rear-view illustration of one embodiment of the fossa lining 108, illustrating the shape of the fossa flange 148 and location and shape of the hole 136, as well as the overall shape of the concave articulating surface 124, which extends the entire lateral length of the inferior surface of the fossa lining 108. The tapered grooved edge 134 of the tab 132 is also illustrated as it tapers outward to match the shape of the slot 130 of the fossa backing 106.

III. Method of Replacement of Fossa Lining

One aspect of the aforementioned embodiments is the ability to remove and replace the fossa lining component 108 after the TMJ replacement prosthesis has been implanted into a patient. The advantage of this fossa sub assembly is that it allows for rapid replacement of the fossa lining 108 without removal of the bone interfacing fossa backing. This benefit is also due to the lateral orientation of the slot and tab of the fossa backing and fossa lining and stabilization screw, which allows the fossa lining and stabilization screw to bel be quickly and easily removed from the patient's body without interference with any other anatomical body portions or portions of the TMJ prosthesis. This allows for decreased surgery times and faster patient recovery.

Figure 8:
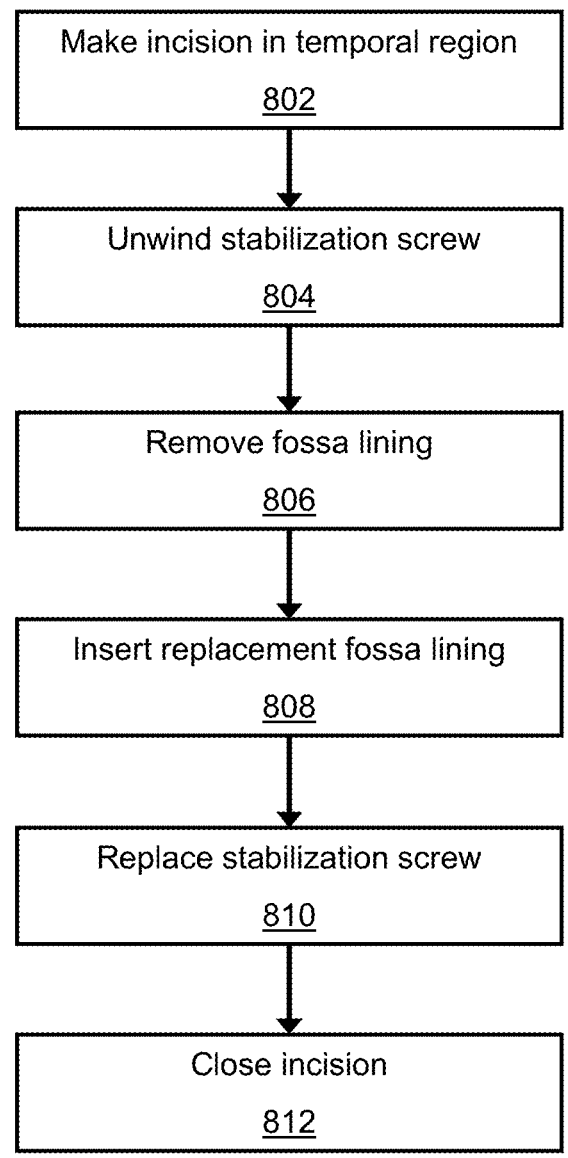
FIG. 8 is a flow diagram illustrating an example process for removing and replacing the fossa lining, according to an embodiment of the invention.

As described in the exemplary method illustrated in the flow diagram of FIG. 8, the orientation and placement of the slots 134 and 142 and stabilization screw 114 allows a surgeon to make a small incision in the temporal bone region of the patient's head (step 802), unwind the stabilization screw (step 804), remove the fossa lining component (step 806) and insert a new replacement fossa lining (step 808). The surgeon may then replace the screw (step 810) and close the patient (step 812).

IV. Articulating Surface Geometry

The articulation point between the condylar head and fossa lining is designed to mimic the shape and function of the natural temporomandibular joint through the design of a uniquely-curved articulating surface on the fossa lining and an oblong curved shape of the condylar head, as will be described in further detail immediately below.

Figure 9:
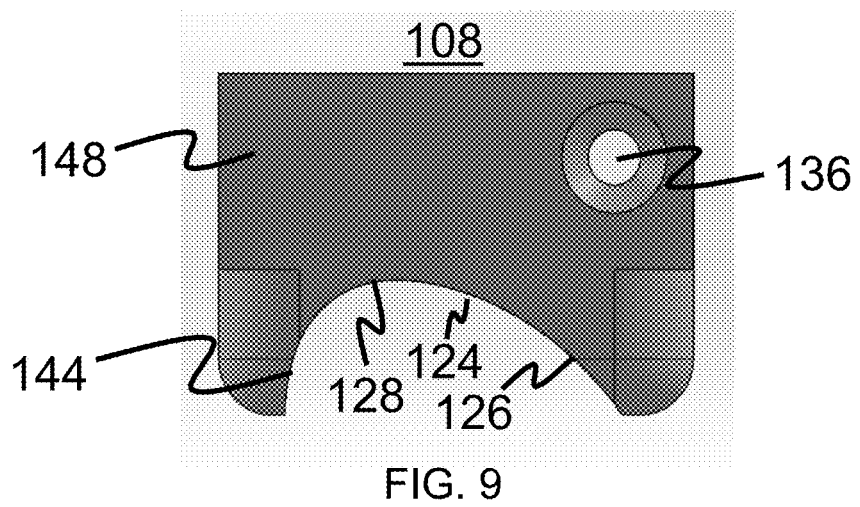
FIG. 9 is a rear-view illustration of the fossa lining, according to an embodiment of the invention.

FIG. 9 is a rear-view illustration along a sagittal plane of one embodiment of the fossa lining 108, more clearly illustrating the geometry of the articulating surface 124. The articulating surface 124 primarily has a gentle curved surface 126 which slowly curves to a high point 128 posterior to a center of the sagittal plane. After the high point 128, the curved surface 124 continues at a significantly steeper slope 144 toward an inferior edge, which additionally helps to retain the condylar head at a position more suited for natural anterior movement of the joint, as illustrated more clearly in FIG. 17, below.

Figure 10:
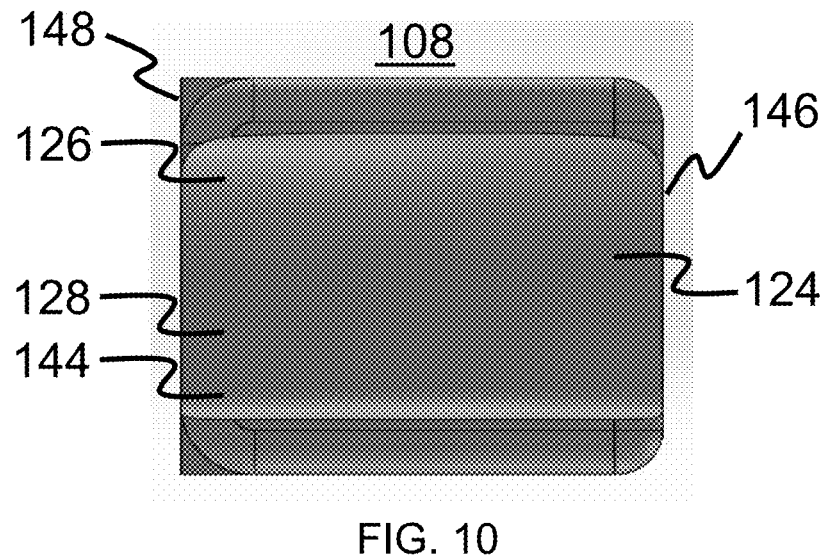
FIG. 10 is an inferior-view illustration of the fossa lining, according to an embodiment of the invention.

FIG. 10 is an inferior-view illustration of the fossa lining 108 showing the overall length of the articulating surface 124 extending from a back portion corresponding to the fossa flange 148 to a front edge 146. The gentle curved surface 126, apex 128 and steep curved surface 144 are identified for better understanding of the overall articulation points of the fossa lining.

Figure 11:
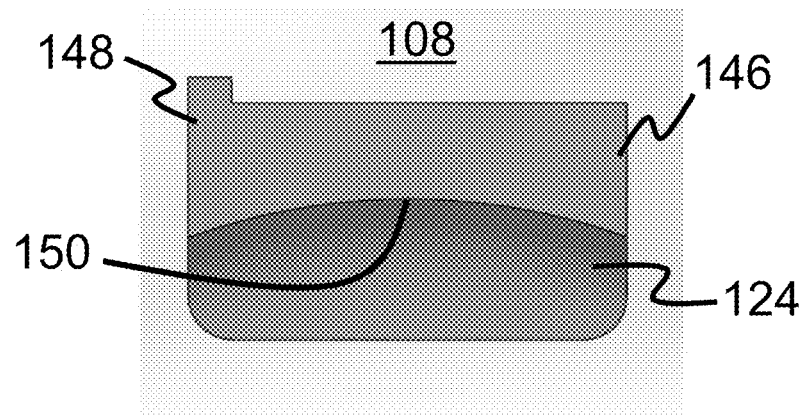
FIG. 11 is a side cross-sectional view illustration of the fossa lining, according to an embodiment of the invention.

FIG. 11 is a side cross-sectional view illustration of one embodiment of the fossa lining 108, illustrating an apex 150 of the articulating surface 124 at a center of the fossa lining in a coronal plane as the curvature extends from a front edge 146 to the fossa flange 148 on the rear edge.

V. Condyle & Condylar Head Geometry

Figure 12:
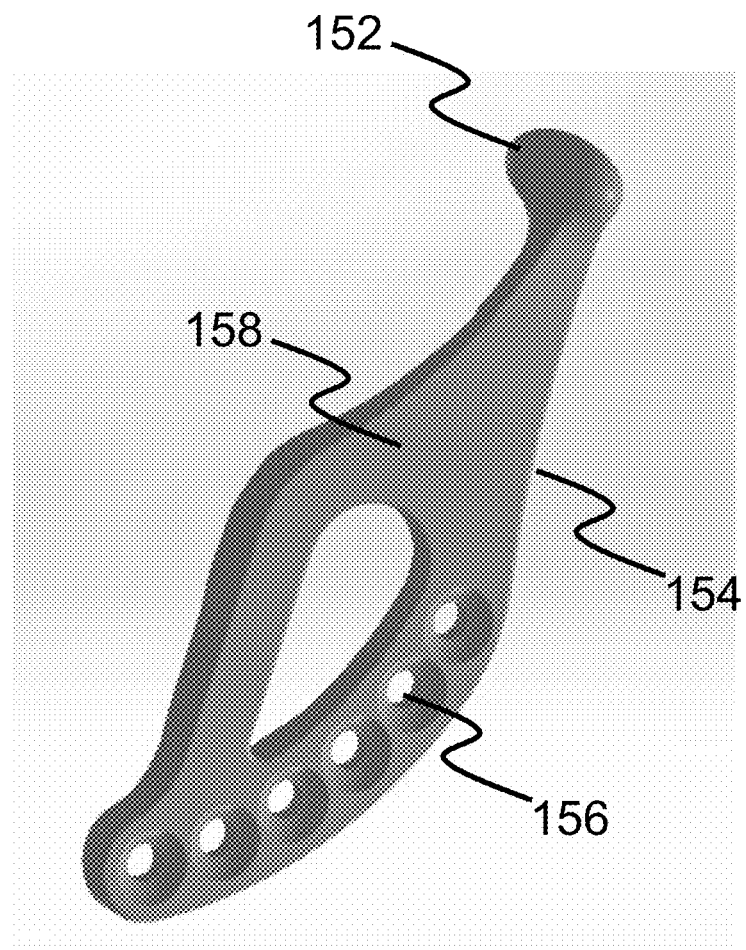
FIG. 12 is a perspective view illustration of an outer surface of a condylar component of the temporomandibular joint replacement, according to one embodiment of the invention.

As illustrated in FIG. 12, in one embodiment the condyle component 104 has a rounded, oblong head 152 designed to fit into the articulating surface 124 of the fossa lining. The condylar component 104 extends away from the head 152 to form a body portion 154 which may be attached to a ramus 116 of the mandibular bone, as illustrated in FIG. 1. The body portion 154 may be secured to the ramus via a series of bone screws positioned through holes 156 in the body portion 154, with the locations being customized to the patient's anatomy. In one embodiment, approximately five to eight holes may be provided.

Figure 13:
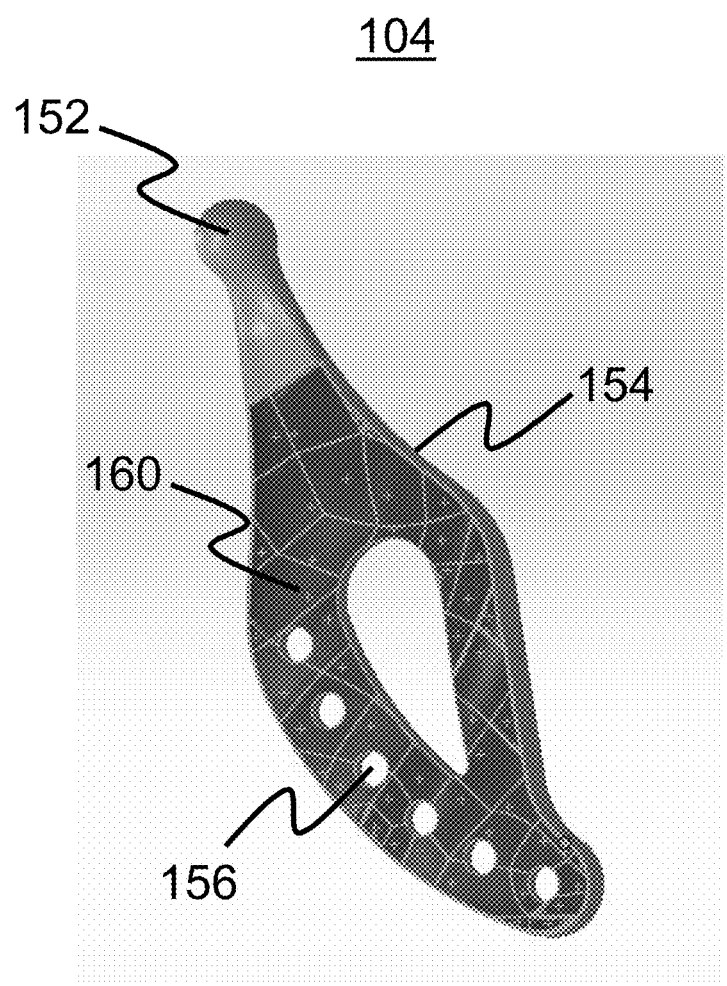
FIG. 13 is a perspective view illustration of an interior surface of the condylar component, according to an embodiment of the invention.

FIG. 12 illustrates an outer surface 158 of the condyle component 104, while FIG. 13 illustrates an interior surface 160 of the condyle component which faces the bone and is therefore contoured to fit an individual patient. Additionally, the interior surface 160 may also have a roughened surface to encourage osseointegration with the bone surface it is adjacent with.

Figure 14:
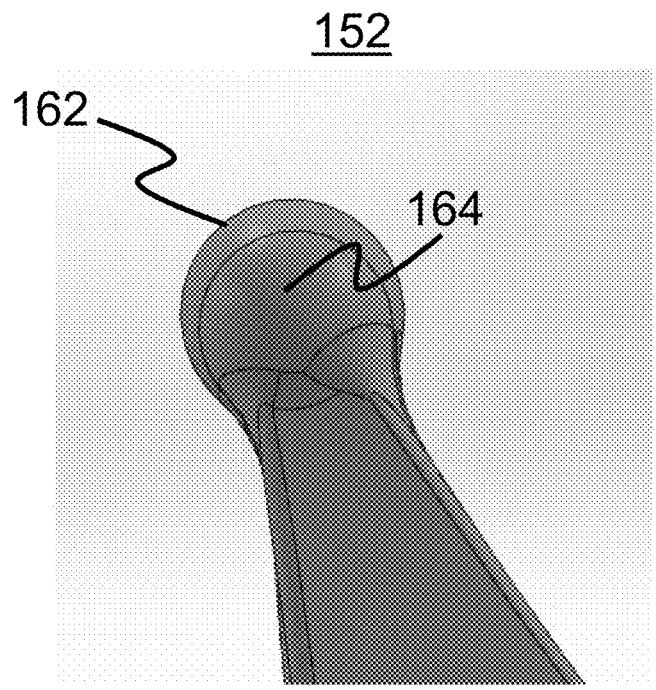
FIG. 14 is a side view illustration of a condylar head, according to an embodiment of the invention.
Figure 15:
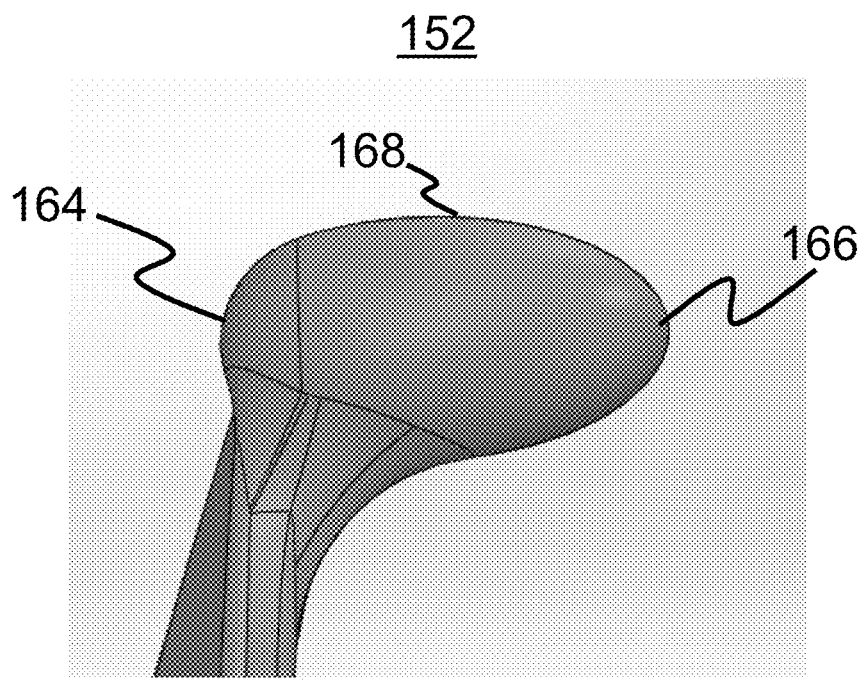
FIG. 15 is a front view illustration of the condylar head, according to one embodiment of the invention.

FIG. 14 is a side view illustration of a condylar head 152 along a sagittal plane, illustrating the overall spherical curvature 162 of the condylar head as viewed from the side perspective of directly viewing a left side 164 of the condylar head 152. In contrast, FIG. 15 is a front view illustration of the condylar head 152 viewed along a coronal plane, illustrating the oblong shape 168 of the condylar head as it extends from the left side 164 to a right side 166. The condylar head 152 is shaped to provide for rotation of the mandible for mastication and to also allow some mediolateral translation via the corresponding curvature and apex 150 of the articulating surface 124 of the fossa lining 106.

VI. Interface of Articulating Surface & Condylar Head

Figure 16:
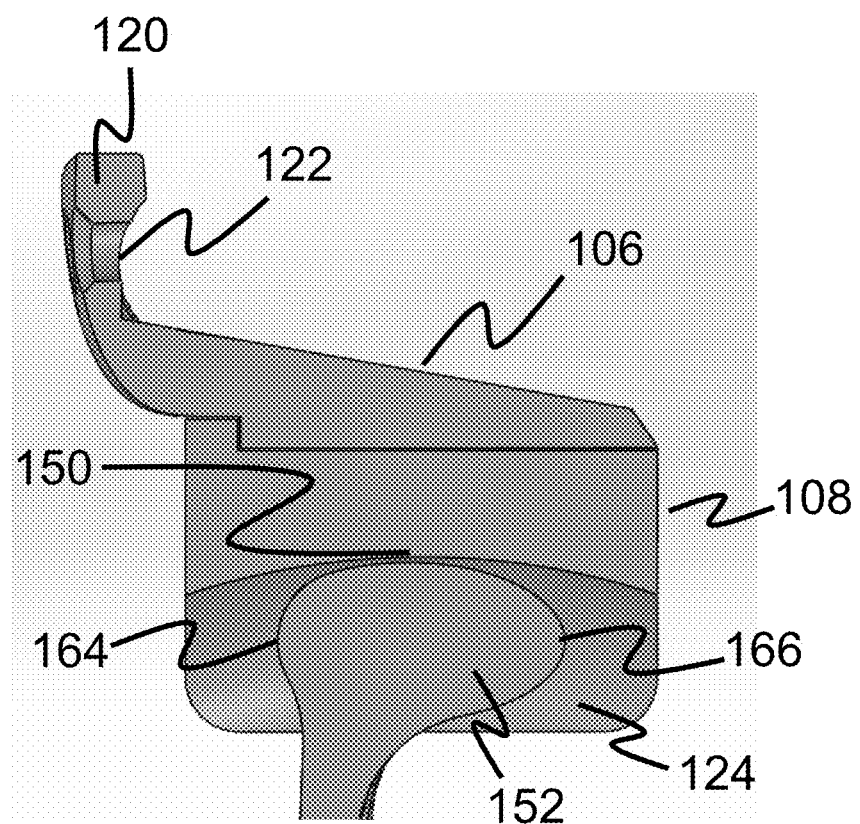
FIG. 16 is a front cutaway view illustration of an articulating joint of the temporomandibular joint replacement, according to one embodiment of the invention.
Figure 17:
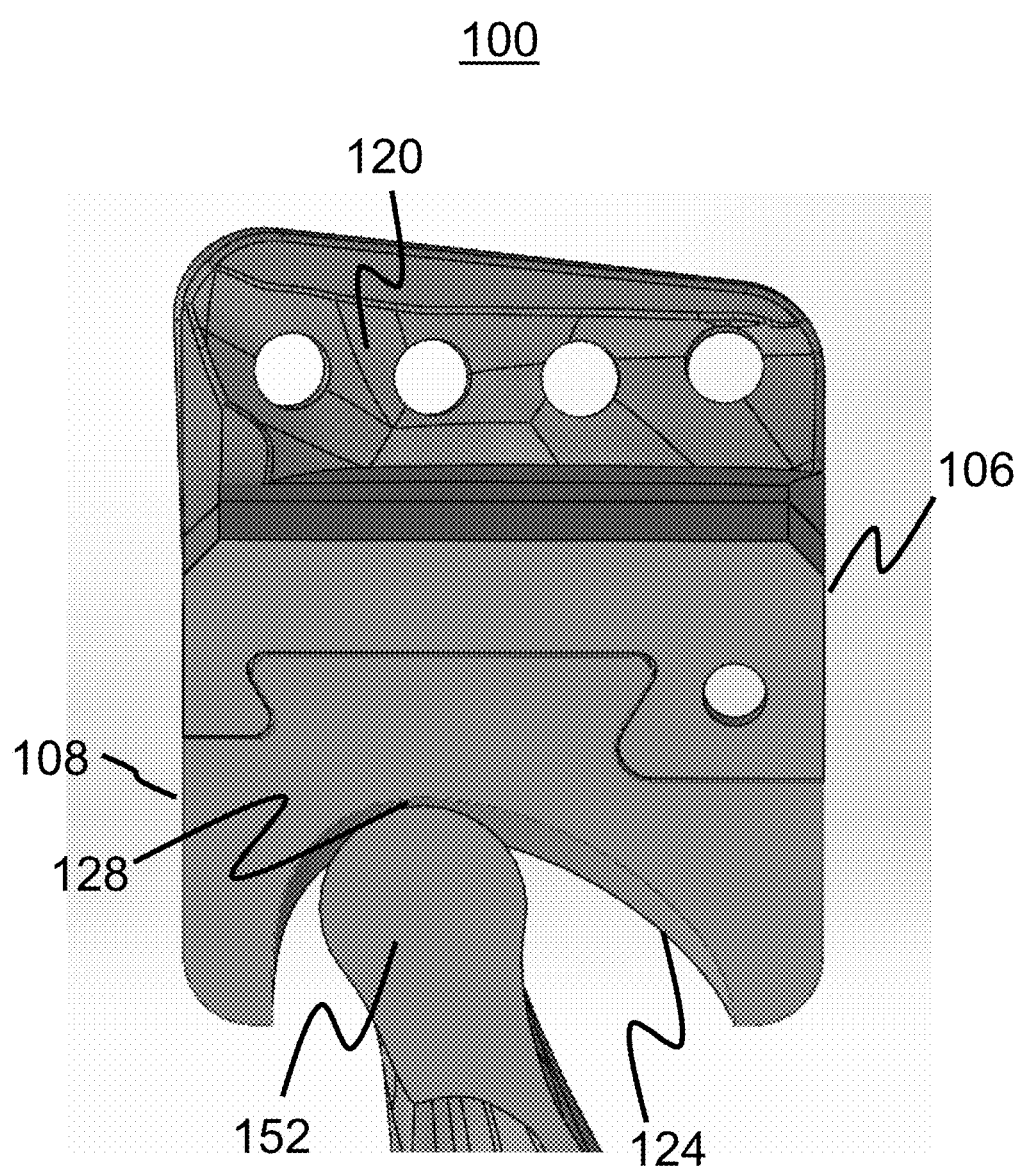
FIG. 17 is a side-view illustration of the articulating joint of the temporomandibular joint replacement, according to one embodiment of the invention.

FIG. 16 is a front cross-sectional front-view illustration of one embodiment of an articulating joint of the temporomandibular joint replacement prosthesis 100, showing the placement of the condylar head 152 into the articulating surface 124 of the fossa lining 108. The condylar head 152 is positioned into the deepest part of the articulating surface 124 along the coronal plane, corresponding to the apex 150 previously illustrated in FIG. 11. FIG. 17 is a cross-sectional side-view illustration of one embodiment of the articulating joint prosthesis 100, further illustrating how the condylar head 152 is also positioned into the deepest part of the articulating surface 124 along the sagittal plane, corresponding to the high point 128 from FIG. 9.

Therefore, the shape of the articulating surface 124 and condylar head 152 maintain the natural occlusion of a patient's teeth, held in place by the patient's existing musculature, which allows for natural movement of the mandible both anteriorly and mediolaterally, restoring function to the jaw.

VII. Materials

The components of the temporomandibular joint replacement prosthesis may vary depending upon the need for the materials to maintain structural integrity of the device, encourage osseointegration with adjacent bone structure, or resist repeated articulation movement. As noted above, the materials should be biocompatible and capable of use with additive manufacturing and milling so that each prosthesis can be anatomically-contoured and textured to each individual patient and corresponding bone structure.

In one embodiment, the fossa backing and condyle component may be manufactured with a titanium alloy such as Ti64 via three-dimensional (3D) printing and milling, with the bone-facing structures such as the interior flange portion 140, seat portion 146 and condyle interior surface 160 being manufactured and/or milled with a roughened surface to encourage osseointegration with the adjacent bone structure. The stabilization screw may also be manufactured with a titanium alloy.

The fossa lining may be manufactured from an ultra-high molecular weight polyethylene (UHMWPE) for use with the interface between the articulating surface of the fossa lining and the condylar head of the condylar component. The UHMWPE retains a smooth articulation surface during the interface with the condylar head.

VIII. Method of Manufacture and Implantation

Figure 18:
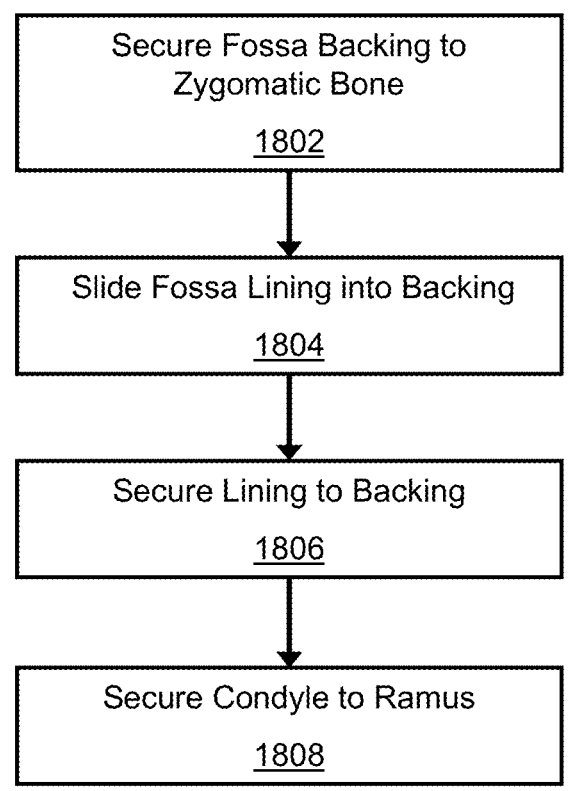
FIG. 18 is a flow diagram illustrating an example process for implanting the annular-shaped subperiosteal jaw prosthesis, according to an embodiment of the invention.

FIG. 18 is a flow diagram of an exemplary method for implanting the temporomandibular joint replacement prosthesis into a patient. In step 1802, a fossa backing is secured to the zygomatic bone via the bone screws, after which, in step 1804, the fossa lining can be attached with the fossa backing via the sliding mechanism provided by the fossa backing grooves and corresponding fossa lining tabs. In step 1806, the fossa lining is secured to the fossa backing, for example with the stabilization screw. In step 1808, the condyle component is attached with a ramus of the mandibular bone to finalize the implantation of the prosthesis.

Figure 19:
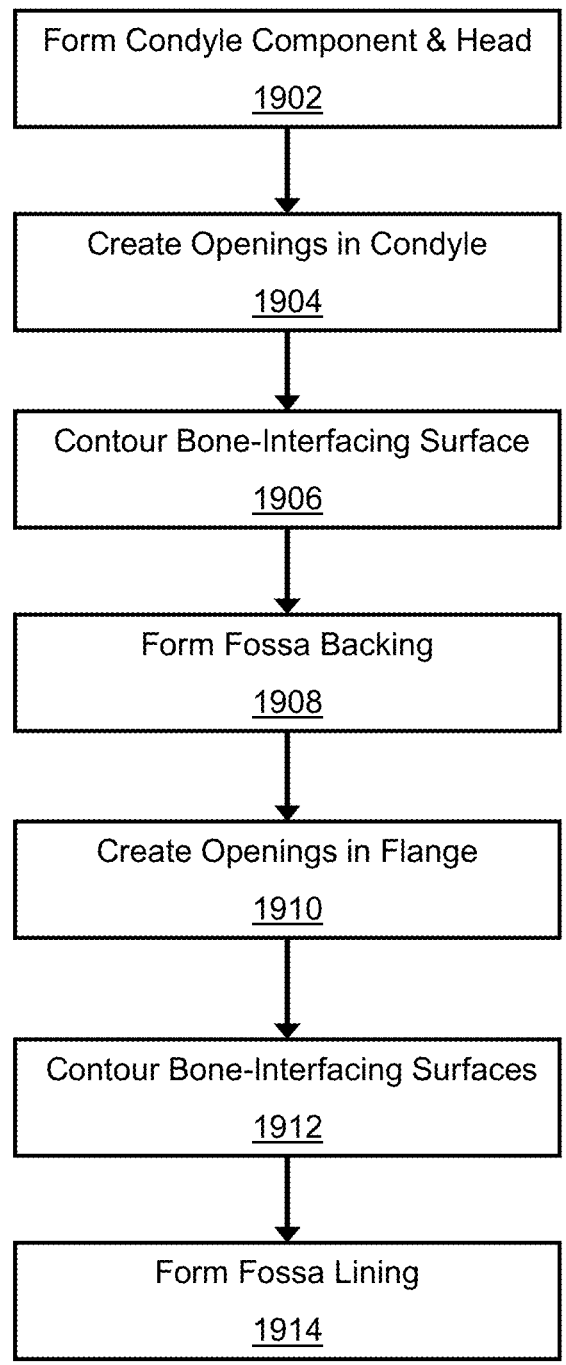
FIG. 19 is a flow diagram illustrating an example process for manufacturing the annular-shaped subperiosteal jaw implant, according to an embodiment of the invention.

FIG. 19 is a flow diagram illustrating an example process for additively manufacturing the temporomandibular joint replacement prosthesis, according to an embodiment of the invention. In a first step 1902, the condylar component including the oblong condylar head is formed in a shape which is anatomically-contoured to an individual patient. In step 1904, one or more openings are formed in a body portion of the condylar component for receiving screws to attach the condylar component with the corresponding bone structure. In step 1906, an interior bone-interfacing surface of the condylar component is contoured to provide for enhanced osseointegration. In step 1908, a fossa backing is formed with a flange portion, slot portion and screw opening. In step 1910, one or more openings are formed in the flange portion for receiving screws to attach the fossa backing with the adjacent zygomatic bone structure. In step 1912, an interior surface of the flange portion and seat portion of the fossa backing is contoured to provide for enhanced osseointegration. In step 1914, a fossa lining is formed with a tab portion and concave articulating surface.

As mentioned above, the temporomandibular jaw replacement prosthesis may be additively-manufactured from a biocompatible material so that each implant is anatomically-contoured to an individual patient. This may include the use of Ti64 and UHMWPE, as noted above.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A patient-specific temporomandibular joint replacement comprising:

a condylar component comprising a condylar head and a body portion, the body portion having a mandibular-bone-contacting surface anatomically-contoured for attachment with a mandibular bone; and a fossa component comprising:

a fossa backing having zygomatic-bone-contacting surfaces anatomically-contoured for attachment with a zygomatic bone; and a fossa lining slidably attached with the fossa backing, the fossa lining including an open-ended concave articulating surface which interfaces and articulates with the condylar head of the condylar component, wherein the fossa backing and fossa lining are slidably attached via slots on the fossa backing which fit corresponding tabs on the fossa lining, wherein the articulating surface of the fossa lining curves to a high point posterior of a center of a sagittal plane and apexes at a center of the fossa lining in a coronal plane, wherein the condylar head of the condylar component has an overall spherical or rounded shape along a sagittal plane and an overall oblong shape along a coronal plane, and wherein the oblong shape of the condylar head is oriented laterally within the articulating surface of the fossa lining.

2. The temporomandibular joint replacement of claim 1, wherein the slidable attachment is laterally oriented in a substantially perpendicular orientation with respect to the zygomatic bone.

3. The temporomandibular joint replacement of claim 2, wherein the fossa lining is secured with the fossa backing via a stabilization screw.

4. The temporomandibular joint replacement of claim 1, wherein the zygomatic-bone-contacting surfaces of the fossa backing are formed from a titanium alloy.

5. The temporomandibular joint replacement of claim 1, wherein the zygomatic-bone-contacting surfaces of the fossa backing have a roughened surface.

6. The temporomandibular joint replacement of claim 1, wherein the articulating surface of the fossa lining is formed from an ultra-high molecular weight polyethylene.

* * * * *